US006477403B1

(12) United States Patent
Eguchi et al.

(10) Patent No.: US 6,477,403 B1
(45) Date of Patent: Nov. 5, 2002

(54) ENDOSCOPE SYSTEM

(75) Inventors: Masaru Eguchi; Koichi Furusawa, both of Tokyo; Shinsuke Okada, Saitama-ken; Ryo Ozawa, Tokyo; Tetsuya Nakamura; Tetsuya Utsui, both of Saitama-ken, all of (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 21 days.

(21) Appl. No.: 09/634,549

(22) Filed: Aug. 8, 2000

(30) Foreign Application Priority Data

Aug. 9, 1999 (JP) ............................................ 11-225055

(51) Int. Cl.⁷ .................................................. A61B 6/00
(52) U.S. Cl. ........................ 600/478; 600/476; 600/101; 600/182; 356/450; 356/456; 356/477
(58) Field of Search ................................. 356/345, 357, 356/360, 358, 355, 359, 121, 123, 124; 250/227.19, 227.27, 227.26, 227.2; 600/310, 407, 473, 476, 478, 101, 111, 112, 117, 153, 160, 163, 166, 167, 102, 245–248

(56) References Cited

U.S. PATENT DOCUMENTS 5,321,501 A   6/1994   Swanson et al.
5,459,570 A   10/1995  Swanson et al.
6,002,480 A * 12/1999  Izatt et al. .................. 356/345
6,216,540 B1 * 4/2001  Nelson et al. ................. 73/633

FOREIGN PATENT DOCUMENTS

JP          6154228        6/1994

* cited by examiner

Primary Examiner—Marvin M. Lateef
Assistant Examiner—Jeoyuh Lin
(74) Attorney, Agent, or Firm—Greenblum & Bernstein, P.L.C.

(57) ABSTRACT

An endoscope system is provided with first and second light guides, which are optically coupled by an optical coupler. A low-coherent light source is provided, and the light emitted therefrom is incident on the first or second light guide. Further provided is a scanning unit that causes the light beam emerged from the first light guide to scan on a predetermined surface of the object. The light beam reflected by the object is directed, by the scanning unit, to the first light guide as a detection light beam. A light beam emerged from the second light guide is reflected by a reflector and returned to the second light guide as a reference beam. By varying the optical path length of the reference beam relative to that of the detection beam, two beams interfere. A signal processing system generates OCT image based on the signal detected by a light detecting device which receives the interfering beams.

12 Claims, 7 Drawing Sheets

ENDOSCOPE SYSTEM

BACKGROUND OF THE INVENTION

The present invention relates to an endoscope system that is capable of capturing in vivo OCT (Optical Coherence Tomography) images of an object.

Conventionally, endoscopic devices for observing objects inside a human cavity have been known. Such an endoscope is provided with an endoscope to be inserted inside the human cavity, and an illuminative external device, which is to be connected to the endoscope. The external device includes a light source unit for illuminating the object and a processor for processing image signals.

The endoscope includes:

an illuminating optical system, which is connected to the light source unit of the external device and used for illuminating an object (e.g., the paries of a body cavity);

an objective optical system for forming an optical image of the object; and a CCD (Charge Coupled Device) provided substantially at a focal plane of the objective optical system and electrically connected to the processor of the external device.

At a tip end of the endoscope, an instrument opening is formed. Forceps or various kinds of treatment instruments inserted in the endoscope are protruded from the instrument opening inside the human cavity.

With the endoscope system described above, an operator is capable of observing inside the human cavity. The operator firstly inserts the endoscope inside the human cavity. Light emitted by the light source unit of the external device is projected to an object to be observed through the illuminating optical system. An optical image of the illuminated object is formed, through the objective optical system, on the light receiving surface of the CCD. The CCD converts the received optical image into an electronic image (i.e., image signal), which is transmitted to the processor of the external device. The processor processes the received image signal, and display the image of the object on a displaying device. Thus, the operator is capable of observing inside the human cavity of a patient through the displaying device.

If the operator judged that there is a possibility of a cancer or a tumor with in the observing portion of the human cavity, a forceps or biopsy instrument is inserted in an instrument channel inside the endoscope. The tip portion of the instrument is protruded from the instrument opening, and the tissues of the portion in question can be collected. The tissues thus obtained is subjected to a pathological inspection, and based on the results of the inspection, diagnosis is made.

According to the conventional endoscope system as described above, only the surface of the human cavity is observable. In order to know the condition of tissues beneath the paries of the human cavity, biopsy operation is required. In particular, in order to find an early cancer or a small tumor, the biopsy operation is indispensable. However, the pathological inspection requires time, and therefore, the diagnosis requires time.

Further, in view of a burden to the patient, the biopsy can be done only in a limited area and by a limited number of times. Diseased portion may be present at a portion other than the portion identified by the operator. However, such a portion might be overlooked, and as a result, an accurate diagnosis may not be done even if the pathological inspection is performed.

SUMMARY OF THE INVENTION

It is therefore an object of the present invention to provide an improved endoscope system which enables an accurate diagnosis within a relatively short period of time.

For the object, according to the present invention, there is provided an endoscope system, which is provided with a first light guide, a second light guide, an optical coupler for optically coupling the first and second light guides, a low-coherent light source that emits a low-coherent light beam, the low-coherent light source being provided at a proximal end side of one of the first and second light guides, the light emitted by the low-coherent light source being incident on the one of the first and second light guides, a scanning unit that causes the light beam emerged from the first light guide to scan on a predetermined surface of the object, the scanning unit directing the light beam reflected by the object to the first light guide as a detection light beam, a reflector that reflects a light beam emerged from the second light guide to the second light guide as a reference beam, an optical path length adjusting system that relatively changes a length of an optical path length from the optical coupler to the object via the first light guide and an optical path length from the optical coupler to the reflector via the second light guide, a light detecting device provided at a proximal end side of the other of the first and second light guides, the light detecting device detecting an interfered beam generated due to interference between the reference beam and the detection beam, and a signal processing system that generates a tomogram based on the signal detected by the light detecting device when the optical path length adjusting system and the scanning unit operate.

Optionally, the first light guide includes a plurality of optical paths, the second light guide includes a plurality of optical paths, the number of the optical paths included in the second light guide being equal to the number of the optical path included in the first light guide, the optical coupler couples the plurality of optical paths included in the first light guide with the plurality of optical paths included in the second light guide, respectively. The scanning unit causes the light beams emitted from the plurality of optical paths of the first light guide to be incident on the object with the plurality of light beams being aligned such that a detection line is formed on the object, the scanning unit shifting the detection line in a direction perpendicular to the detection line so as to scan a predetermined two-dimensional area, the plurality of beams reflected by the object being directed to the plurality of optical paths of the first light guide via the scanning unit.

In another case, each of the first and second light guides is composed of a fiber array having a plurality of single-mode optical fibers arranged in parallel.

Optionally, the scanning unit includes a deflector that deflects the plurality of light beams emitted from the tip of the plurality of optical paths of the first light guide toward the object with the plurality of beams aligned in parallel, and shifts the detection line in the direction perpendicular to the detection line with the plurality of beams remained to be aligned in parallel.

In a particular case, each of the first and second light guides includes a single optical path, and wherein the scanning device includes a main scanning device which shifts the incident position of the beam, on the object, emitted by the first light guide in a main scanning direction, and an auxiliary scanning device which shifts the incident position of the beam, on the object, emitted by the first light guide in an auxiliary scanning direction which is perpendicular to the main scanning direction.

Optionally, the signal processing system generates a tomogram of the object, the tomogram corresponding to an area from a surface of the object to a predetermined depth therefrom.

Still optionally, the optical path length adjusting system moves the reflector toward/away from a tip of the second light guide to vary the optical path length from the optical coupler to the reflector via the second light guide relative to the optical path length from the optical coupler to the object via the first light guide.

Preferably, the low-coherent light source includes a super-luminous diode.

Further optionally, the endoscope system may further be provided with an illuminating optical system that emits visible light and/or excitation light which causes biotissues to fluoresce, to the object, an objective optical system that converges the light from the surface of the object to form an object image, and an image capturing system that captures the optical image formed by the objective optical system.

Furthermore, the endoscope system may be provided with a visible light source emitting visible light, an excitation light source emitting the excitation light, a light source switching system that selects one of the visible light and the excitation light and causes the selected one of the visible light and excitation light to be incident on the illuminating optical system. The objective optical system forms a normal light image of the object when the visible light is incident in the illuminating optical system, and the objective optical system forms a fluorescent light image of the object when the excitation light is incident in the illuminating optical system.

Still optionally, the endoscope system may be provided with a displaying device that displays the object image captured by the image capturing system, and the tomogram generated by the signal processing system.

DESCRIPTION OF THE ACCOMPANYING DRAWINGS

DESCRIPTION OF THE EMBODIMENT

Hereinafter, three embodiments according to the present invention will be described with reference to the accompanying drawings.

First Embodiment

Figure 1:
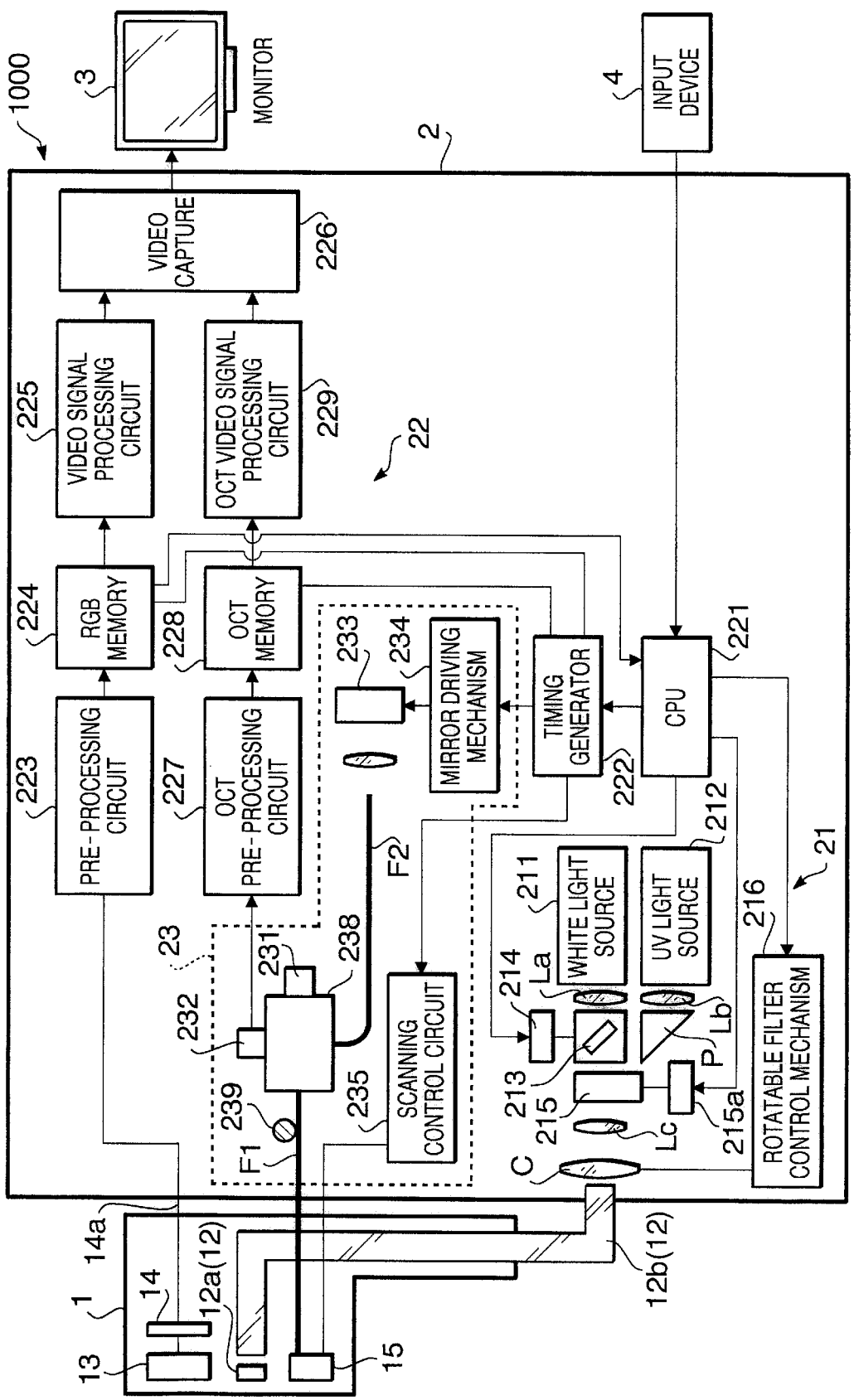
FIG. 1 is a block diagram schematically illustrating an electrical structure of an endoscope system according to a first embodiment of the invention.

FIG. 1 shows an electronic structure of the endoscope system 1000 according to a first embodiment of the invention.

As shown in FIG. 1, the endoscope system 1000 includes an endoscope 1, and external device 2 connected to the endoscope 1, a monitor 3 connected to the external device 2, and an input device 4.

The endoscope 1 includes an insertion tube having an elliptical cross section, and an operation unit which is connected to a proximal end of the insertion tube. Various operation switches are provided on the operation unit.

Inside the insertion tube of the endoscope 1, an illuminating optical system 12, an objective optical system 13, an image capturing system 14, and an OCT scanning system 15 are provided. The illuminating optical system 12 is provided with an illumination lens 12a secured at the tip end of the insertion tube, and a light guide fiber bundle 12b (hereinafter referred to as a light guide). The light guide 12b is inserted through the endoscope 1 and connected to the external device 2.

An objective optical system 13 is provided with an objective lens secured at the tip end of the insertion tube, and a cut-off filter, which shields a UV component of the incident light. The objective optical system 13 converges the incident light on the image receiving surface of the CCD 14 and forms an object image thereon. The CCD 14 outputs an image signal corresponding to the optical image formed on the image receiving surface thereof. The CCD 14 is connected to the external device 12 through a signal line 14a, and the image signal is transmitted to the external device 2.

The structure of the OCT will be described in detail with reference to FIG. 2 later.

The endoscope 1 constructed as above is connected to the external device 2. The external device 2 will be described in detail hereinafter.

As shown in FIG. 1, the external device 2 is provided with a light source unit 21, a processor 22 and an OCT unit 23. The light source unit 21 includes a white light source 211, which emits so-called white light, and a UV light source 212 which emits UV light. The UV light is used as an excitation light for exciting the human tissues to fluoresce. The wavelength of the excitation light is approximately 350 nm though 380 nm, and the wavelength of fluorescent light, which is emitted from the human tissues upon incidence of the excitation light, is approximately 400 nm though 700 nm.

On an optical path of the white light emitted by the white light source 211, a collimating lens La, a switching mirror 213, an aperture stop 215, a condenser lens Lc, and a rotating filter C are arranged in this order. The switching mirror 213 is connected to a light source switching controlling mechanism 214. Specifically, the light source switching mechanism 214 locates the switching mirror 213 at a retracted position, at which the switching mirror is retracted from the optical path of the white light, or an operable position at which the switching mirror shields the white light (i.e., the switching mirror prevents the white light from proceeding to the aperture stop).

The aperture stop 215 is connected to the aperture control mechanism 215a. The aperture stop 215 is controlled by the aperture control mechanism 215a to change the aperture size so as to change the amount of light passed therethrough. The rotatable filter C has a disk like appearance and formed with four fan-shaped filters: RGB color filters (three color filters for red, green and blue components); and a transparent filter. The rotatable filter C is connected to the rotatable filter control mechanism 216. The rotatable filter C is driven by the rotatable filter control mechanism 216 to rotate such that the four filters are sequentially located on an optical path.

The white light emitted by the white light source 211 is collimated by the collimating lens La. If the switching mirror 213 is located at the retracted position, the white light is directed to the aperture stop 215. The white light, light amount 20 of which is adjusted by the aperture stop 215, is converged by the condenser lens Lc, and passes through the rotatable filter C. As described above, the rotatable filter C is rotated by the rotatable filter control mechanism 216 to rotate and the four color filters are sequentially inserted in the optical path. Accordingly, the white light is converted into Blue, Green, Red and white light sequentially, and converged on the proximal end surface of the light guide 12b.

On the optical path of the excitation light emitted by the UV light source 212, the collimating lens Lb and a prism P are arranged in this order. The excitation light emitted by the UV light source 212 is collimated by the collimating lens Lb, reflected by the prism P and is directed to the switching mirror 213. If the switching mirror 213 is located at the operative position (as shown in FIG. 1), it reflects the excitation light toward the aperture stop 215. The excitation, whose light amount is adjusted by the aperture stop 215, is converged by the condenser lens Lc and is directed to the rotatable filter C. In this case, the rotatable filter control mechanism 216 inserts the transparent filter in the optical path and stops rotating the rotatable filter C. Then, the excitation light passes through the transparent filter of the rotatable filter C and is converged on the proximal end surface of the light guide 12b.

Thus, the retracted and operative positions of the switching mirror 213 will be referred to as a normal image observation condition, in which the white light emitted by the white light source 211 is directed to the aperture stop 215, and a fluorescent image observation condition, in which the excitation light emitted by the UV light source 212 is directed to the aperture stop 215. The rotatable filter C rotates to sequentially insert the filters in the optical path so that, in the normal observation condition, the incident white light is converted into blue, green, red and white light. In the fluorescent image observation condition, the transparent filter is fixedly inserted in the optical path.

Next, the processor 22 will be described. The processor 22 includes a CPU 221 and a timing generator 222. The CPU 221 is connected with the light source switching mechanism 214 and the rotatable filter control mechanism 216 of the light source unit 21, the timing generator 222, and the input device 4. The timing generator 222 generates various reference clock signals. Various processing performed by the processor 22 and various operations performed by the OCT unit 23 are executed in accordance with the reference clocks generated by the timing generator 222.

The CPU 221 controls the light source switching mechanism 214 to switch the switching mirror between the normal observation condition and the fluorescent image observation condition, and controls the rotatable filter control mechanism 216 to set the rotatable filter C to the normal image observation condition or the fluorescent image observation condition. Specifically, a switch for selecting the normal image observation and fluorescent image observation is provided on an operation unit of the endoscope 1. The CPU 221 detects the operation status of the selecting switch, controls the light source switching mechanism 214 and the rotatable filter control mechanism 216 so that the switching mirror 213 and the rotatable filter C are set to one of the normal image observation condition and the fluorescent image observation condition selected by the selecting switch. Further, the CPU 221 controls the aperture control mechanism 215a, based on a signal transmitted from an RGB memory, which will be described later, to adjust the aperture size of the aperture stop 215.

The CPU 221, on the other hand, controls the operations executed by the processor 22 and the operations executed by the OCT unit 23 via the timing generator 222.

Further, the processor 22 is provided with a pre-processor 223 connected to the CCD 14 through the signal line 14a, an RGB memory 224, an image signal processing circuit 225 and a video capture 226 connected to the monitor 3.

When the switching mirror 213 and the rotatable filter C are set to the normal image observation condition, the pre-processor 223 retains image signals output by the CCD 14 when the blue, green and red components of light are emitted from the illuminating lens 12a, and discards the image signal when the white light is emitted by the illuminating lens 12a. The pre-processing circuit 223 retains the image signals transmitted from the CCD 14, processes the image signals, applies A/D (analog-to-digital) conversion, and store the digital image signal in the RGB memory 224. It should be noted the blue, green and red components of the image data are stored in the blue, green and red image areas of the RGB memory 224, respectively.

When the switching mirror 213 and the rotatable filter C are set to the fluorescent image observation setting, the pre-processor 223 retains the image signal transmitted by the CCD 14, processes the image signal, applies the A/D conversion, and stores the digital image signal in the all component areas of the RGB memory 224, simultaneously.

The video signal processing circuit 225 retrieves the data stored in the RGB memory 224 at a predetermined timing and processes the same to generate a video signal, which is transmitted to the video capture 226. The video capture 226 displays the obtained video signal on the monitor 3.

The processor 22 further includes an OCT pre-processor 227 connected to the OCT unit 223, an OCT memory 228, and an OCT video signal processor 229. The OCT pre-processor 227 processes the signal transmitted from the OTC unit 23, applies the A/D conversion, and stores the data in the OCT memory 228. The OCT video signal processing circuit 229 retrieves the data stored in the OCT memory 228 at a predetermined timing to generate a video signal, which is transmitted to the video capture 226. The video capture 226 displays the obtained video signal on the monitor 3.

Hereinafter, the OCT unit 23 will be described in detail.

Figure 2:
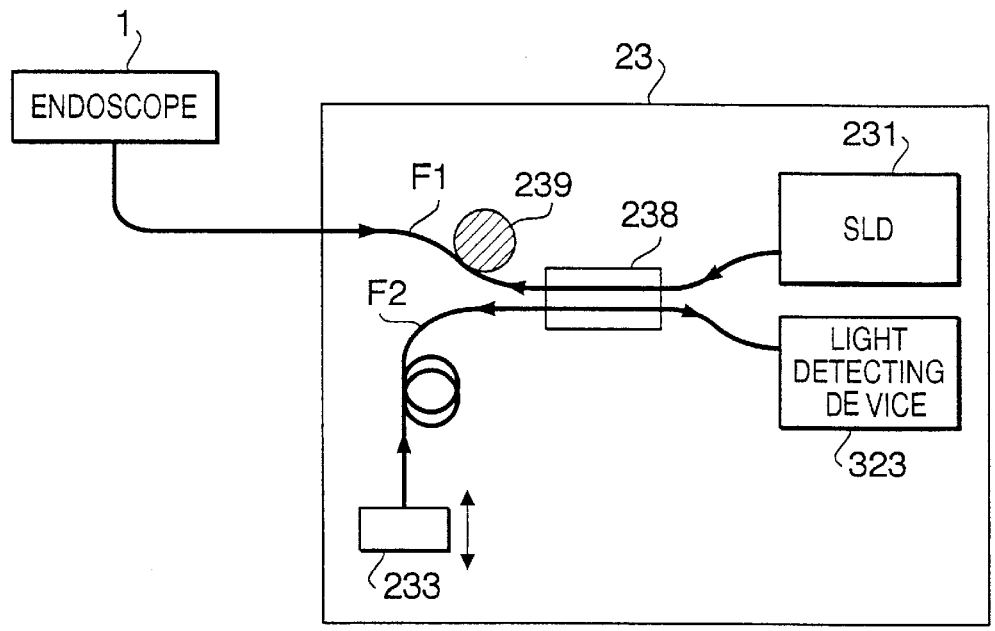
FIG. 2 shows optical paths of the OCT unit.

FIG. 2 shows the optical path of the OCT unit 23. The OCT unit 23 is used for capturing OCT images of the paries of the human cavity. The OCT unit 23 includes a super-luminescent diode (SLD) 231, a light detecting device 232, a reference mirror 233, a mirror driving mechanism 234 and a scanning control circuit 235.

The SLD 231 is a light source emitting a low-coherent light beam at a near-infrared range. The coherent distance of the light beam emitted by the SLD 231 is very short, e.g., in the order of 10 $\mu$m through 1000 $\mu$m. The light detecting device 232 is connected to a pre-processing circuit 227 of the processor 22.

The mirror driving mechanism 234 is for moving the reference mirror 233 at a high speed. The mirror driving mechanism 234 is connected to the timing generator 222 in the processor 22. The scanning control circuit 235 is connected the OCT scanning unit 15 of the endoscope 1, and to the timing generator 222.

Further, the OCT 23 includes a first light guide path F1, a second light guide path F2, an optical coupler 238, and a piezo modulating element 239. As will be described, each of the light guide paths F1 and F2 is formed by a fiber array including a plurality of optical paths. For the sake of simplicity, description will be made by assuming that each light guide paths F1 and F2 has a single optical path.

The first light guide path F1 is arranged such that the proximal end thereof faces the SLD 231. The first light guide F1 is inserted through the endoscope 1 and the tip end of the first light guide F1 faces the OCT scanning unit 15. The second light guide F2 is arranged such that the proximal end thereof faces the light detecting device 232. The tip end of the second light guide F2 faces the reference mirror 233. It should be noted that the reference mirror 233 is constructed to reciprocate along the axis of the light guide F2.

The light guides F1 and F2 are optically coupled using the optical coupler 238. An optical distance, in the first light guide F1, from the optical coupler 238 to the tip end thereof, and an optical distance, in the second light guide F2, from the optical coupler 238 to the tip end thereof are configured to be the same. Further, the first guide F1 is wound around the piezo modulation element 239 having a cylindrical shape, at a portion from the optical coupler to the tip end thereof. The piezo modulation element 239 expands and shrinks in the radial direction at high speed so that the frequency and phase of the light passing through the light guide F1 is modulated.

It should be noted that the SLD 231, the light detector 232, the reference mirror 233, the light guides F1 and F2, and the optical coupler 238 are arranged as described above to form the Michelson interferometer.

The OCT unit 23 is capable of capturing OCT images of an object (e.g., paries of the human cavity), with the tip end portion of the insertion tube facing the object.

The low-coherent light emitted by the SLD 231 is incident on the first light guide F1, and split by the optical coupler 238 into the light proceeds along the first light guide F1 to the tip end thereof, and the light proceeds along the second light guide F2 to the tip end thereof. The light directed by the first light guide F1 is deflected by the scanning unit 15 of the endoscope 1, and emerged therefrom as a scanning light beam. The scanning light beam emerged from the endoscope 1 is reflected by various tissues on and inside the paries of the human cavity. The reflected light beam enters the endoscope 1, and directed to the optical coupler 238, through the first light guide F1, through the OCT scanning unit 15 as a detection beam.

The light beam directed by the second light guide F2 is emerged from its tip end and reflected by the reference mirror 233. The light beam reflected by the reference mirror 233 is incident on the second light guide F2 again, and proceeds toward the optical coupler 238 as a reference light beam.

The detection light beam transmitted through the light guide F1 and the reference light beam transmitted through the light guide F2 interfere at the optical coupler 238. It should be noted, however, that the detection beam is a beam reflected by each layer of the biotissues forming the body cavity, it reaches the optical coupler with some delays.

On the other hand, the reference beam is reflected by the reference mirror 233, and therefore, reaches the optical coupler 238 at a fixed timing. Accordingly, from among the various detection beams reflected at various layers of the biotissues, only a beam traveled along an optical path whose length is the same as the optical length of the beam which proceeds from the optical coupler 238 to the reference mirror 233 through the second light guide F2 and then returns therefrom to the optical coupler 238. Thus, from among the detection beams, one which is reflected by a certain one of the layers beneath the paries interferes with the reference light beam.

The interfering beams proceed from the optical coupler 238 through the second light guide F2, and detected by the light detecting device 232. If the mirror driving mechanism 234 changes a position of the reference mirror 233 along the axis of the light guide F2, the optical path length of the reference light beam changes. In such a case, a detection beam interferes with the reference beam changes, i.e., a layer subjected to detection changes. In other words, a depth beneath the paries subjected to detection changes.

Depending on the condition of the biotissues beneath the paries, distribution of intensity of light varies. Thus, depending on the distribution of intensity of light, from the surface of the paries to a layer at a predetermined depth therefrom, tomogram can be obtained.

As described above, the light detecting device 232 outputs the interfering light beams as an electrical signal, and light beams which do not interfere with the reference light as a noise. If a signal-to-noise (S/N) ratio is relatively low, an accurate signal detection cannot be performed. Therefore, in order to raise the S/N ratio, a so-called heterodyne detection method is utilized. That is, the light beam passing through the first light guide F1 is modified, by the piezo modulating element 239, in terms of its frequency and phase. As a result of this modification, the frequency and the phase of the detection light beam slightly shifts with respect to those of the reference light beam. Therefore, the interfered light includes beat. When the light detection device 232 receives the interfered light including the beat, it outputs a beat signal.

The pre-processing circuit 227 of the processor 22 demodulate the beat signal output by the light detection device 232 to derive the signal component accurately. The demodulated signal is A/D (analog-to-digital) converted by the pre-processing circuit 227 and stored in the OCT memory 228.

Each of the light guides F1 and F2 is a fiber array composed of a bundle of hundreds of single-mode optical fibers. The SLD 231 is capable of emitting low-coherent light to the bundle of optical fibers at the same time. The light detecting device 232 is composed of a line sensor, which is capable of detecting the interfering beams transmitted through the bundle of optical fibers individually.

The optical coupler 238 optically couples the optical fibers of the first light guide (fiber array) F1 and those of the second light guide (fiber array) F2, respectively. Specifically, the optical coupler 238 is composed of a multi-channel optical fiber coupler at which corresponding optical fibers of the light guides F1 and F2 are fusion bonded, respectively, with one-to-one correspondence. The optical coupler 238 may be replaced with a beam splitter prism.

As described above, the OCT unit 23 is configured to have a multi-channel (i.e., hundreds of channels) structure, and when connected to the OCT scanning unit 15, for hundreds of detection points on detection lines mutually formed on the object, scanning can be performed in the depth direction.

The scanning operation will be described in detail with reference to FIGS. 3, 4 and 5.

Figure 3:
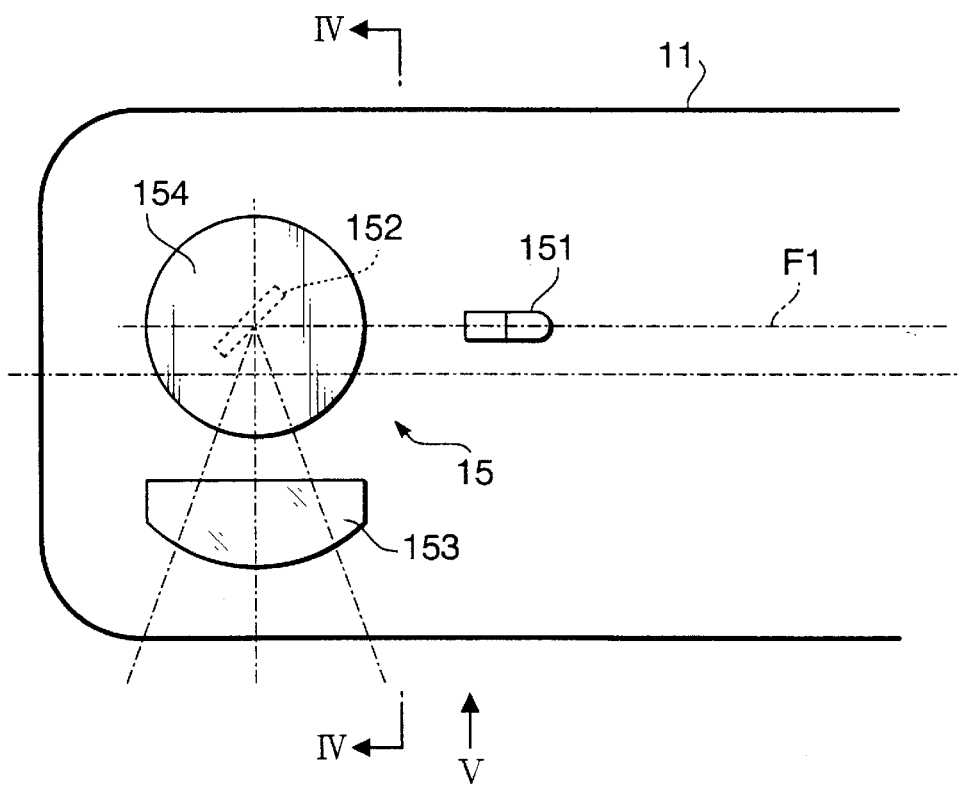
FIG. 3 shows a structure of the OCT scanning unit according to the first embodiment of the invention.
Figure 4:
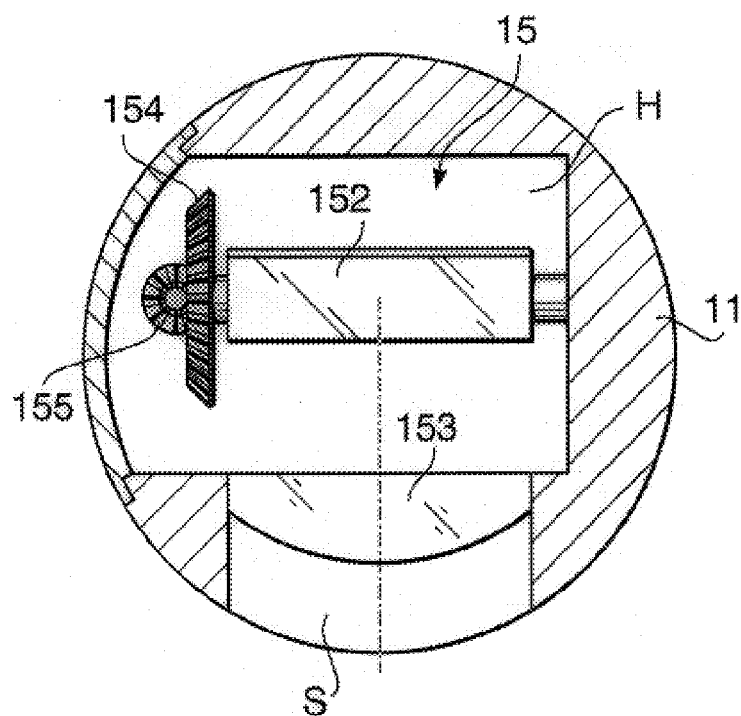
FIG. 4 is a cross section vies of the OCT scanning unit taken along line IV—IV of FIG. 3.
Figure 5:
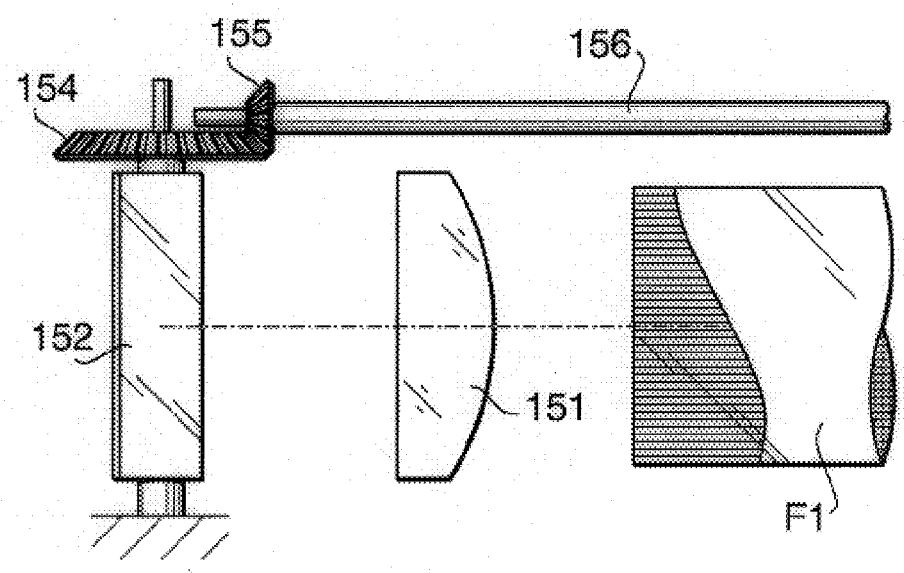
FIG. 5 is a side view of the OCT scanning unit viewed from arrow V of FIG. 3.

FIG. 3 shows across section of a tip portion of the endoscope 1 taken along a plane parallel to the axis thereof, and FIG. 4 is a cross section taken along line IV—IV of FIG. 3. FIG. 5 is a side view viewed along a direction V indicated in FIG. 3. The insertion tube of the endoscope 1 has a case 11, which has a substantially cylindrical outer shape at the tip end portion thereof. In FIG. 3, the case 11 is schematically shown, and in FIG. 5 the case 11 is omitted.

The tip end surface of the case 11 is formed such that the peripheral portion is smoothly beveled. Inside the case 11, an accommodation chamber H is defined. The OCT scanning unit 15 is accommodated in the accommodation chamber H. On a side surface of the case 11, at the tip end portion thereof, a scanning window S communicating with the accommodation chamber H is formed.

The first fiber array F1 of the OCT unit 23 is inserted through the endoscope 1, and the tip end thereof is introduced inside the accommodation chamber H. The tip end portion of the fiber array F1 is arranged such that the axis of each optical fiber extends in parallel with the central axis of the case 11, and the tip end surface thereof is parallel with, and spaced from the tip end surface of the case 11 by a predetermined amount.

The OCT scanning unit 15 inside the accommodation chamber H includes a collimating lens 151, a scanning mirror 152 and an fθ lens 153, on an optical axis, from a fiber array F1 side.

The collimating lens 151 is a rotationally symmetrical plano-convex lens having a shape of a substantially rectangular solid except that one refraction surface is a convex surface. Thus, four side surfaces of the collimating lens 151 are formed to be two pairs of rectangular surfaces. A distance between one pair of the side surfaces (opposite surfaces) having wider area than the other is wider than the width of the fiber array F1.

The collimating lens 151 is arranged such that the focal point on a convex surface side coincides with the center of the light emerging end surface of the fiber array F1, with the wider pair of the side surfaces being arranged in parallel with a plane on which the fiber array F1 is arranged, and the optical axis of the collimating lens is parallel with the axis of the fiber array F1. Therefore, the collimating lens 151 collimates each of the light beams emitted from each optical fiber of the fiber array F1. The principal ray of the central fiber of the fiber array F1 coincides with the optical axis of the collimating lens 151. However, principal rays of the other fibers intersect with the optical axis of the collimating lens at the object side focusing point (exit pupil) of the collimating lens 151. The exit pupil coincides with the center of the scanning mirror 152.

The scanning mirror 152 has a substantially rectangular mirror surface, a length of a longitudinal side thereof being substantially the same as the width of the collimating lens 151. The scanning mirror 152 is supported, at both ends thereof, so as to be rotatable about the center of the mirror surface. The central axis of the mirror surface on the same plane on which the fiber array F1 is arranged, and perpendicular to the central axis of the case 11.

At one end of the scanning mirror 152, a bevel gear 154 is secured. The bevel gear 154 is engaged with another bevel gear 155, which is fixed on a shaft 156 extending parallel with the central axis of the case 11. The shaft 156 is connected to a scanning motor (not shown).

The fθ lens 153 (not shown in FIG. 5) has a shape such that a rotationally symmetrical plano-convex lens is filed with a coaxial rectangular solid filing member. The fθ lens 153, together with the collimating lens 151, constitutes an a focal optical system.

The fθ lens 153 is arranged such that the convex surface is directed outside the endoscope 1, and fitted in the scanning window S. The optical axis of the fθ lens 153 is perpendicular to the plane on which the fiber array F1 is arranged. The fθ lens 153 converges each of the parallel beams reflected by the scanning mirror 152 on a line perpendicular to the surface of FIG. 3, outside the endoscope 1, at an even interval.

With the above construction of the OCT scanning unit 15, each light beam, which is a diverging beam, emitted by each fiber of the fiber array F1 is directed to the collimating lens 151, with the principal rays aligned on a same plane. The collimating lens 151 collimates the incident beams, and emits the collimated beams with inclined toward the optical axis.

A principal ray of each parallel beam emitted by the collimating lens 151 intersects with the optical axis at the center of the scanning mirror 152. Therefore, downstream of the scanning mirror 152, an arrangement of the parallel beams is reversed (in FIG. 5, the arrangement in the up-and-down direction is reversed). The parallel light beams reflected by the scanning mirror 152 are directed to the fθ lens 153. The fθ lens 153 converges the incident beams on a predetermined line outside the endoscope 1 and are arranged evenly spaced from each other.

If the scanning window S is located to face the paries of the human cavity, the light beams emitted from the fθ lens 153 are reflected by the paries. The reflected beams returns, i.e., proceeds the fθ lens 153, scanning mirror 152, and the collimating lens 151 in this order, and then incident on the optical fibers of the fiber array F1, respectively.

In the present embodiment, the multi-channel OCT unit 23 is employed. Therefore, for the detection points, the number of which is the same as the number of the channels, detection is performed simultaneously. That is, on a mutually formed detection line on the object, detection is performed for hundreds of detection points simultaneously.

The detection in a direction perpendicular to the mutual line is performed by rotating the scanning mirror 152. Specifically, when the scanning motor (not shown) rotates the shaft 156, the bevel gear 155 rotates the other bevel gear 154, thereby the scanning mirror 152 rotated. As the scanning mirror 152 rotates, the mutual line shifts in the direction perpendicular to the extending direction of the mutual line. Therefore, on the paries, a rectangular area is scanned sequentially. It should be noted that, by rotating the scanning motor in forward and reverse directions repeatedly, the scanning mirror 152 is driven to rotate reciprocally within a predetermined rotational range. With this control, the OCT scanning unit 15 can continuously and repeatedly scan the rectangular scanning area facing the scanning window S.

It should be noted that, although it is not shown, on the side surface of the case 11, adjacent to the scanning window S (on the proximal end side), an illuminating lens 12a of the illuminating optical system 12, and an objective lens (not shown) of an objective lens system 13 are fitted.

Operation of the endoscope system constructed as above will be described.

When an operator turns ON the external device 2, the white light source 211 and the UV light source 212 are turned ON. The switching mirror 213 and the rotatable filter C are, at the initial stage, positioned at the normal observation positions. Therefore, the white light emitted by the white light source 211 reaches the aperture stop 215 and the condenser lens Lc.

The rotatable filter control mechanism 216 sequentially insert the filters of the rotational filter C, the white light emerged from the condenser lens Lc is changed to Blue, Green, Red and white light sequentially, and then converged on the proximal side end surface of the light guide 12b. The light converged on the light guide 12b is directed thereby and emitted from the illuminating lens 12a. That is, from the illuminating lens 12a, the Blue light, Green light, Red light and the white light is emitted sequentially.

If the operator inserts the insertion tube 11 of the endoscope 1 inside the human cavity, and the illuminating lens 12a of the illuminating optical system 12, the objective lens 13a of the objective optical system 13 and the scanning window S face the paries of the human cavity to be observed, the light emitted from the illuminating lens 12a sequentially illuminates the paries.

Then, the paries sequentially illuminated by the blue, green, red and white light, image of the corresponding color components are formed on the image receiving surface of the CCD 14 by the objective optical system 13. Then, the CCD 14 converts the optical image into the electric image, and the electrical image (i.e., the image signal) is transmitted to the pre-processing circuit 223. The pre-processing circuit 223 retains the image signals obtained when the blue, green and red light is emitted from the illuminating lens 12a, and the image signal obtained when the white light is emitted was abandoned.

The pre-processing circuit 223 applies signal processing to the retained image signals, and then performs the A/D conversion. The image data (i.e., A/D converted image data) thus obtained is stored to B, G and R areas of the RGB memory 224, in this order. Specifically, the image data obtained when the Blue light is emitted from the illuminating lens 12a is stored in the B area of the RGB memory 224. Similar procedure is performed for the data obtained when the Green light, and the Red light are emitted from the illuminating lens 12a.

The image signal processing circuit 225 retrieves the data stored in the RGB memory 224 at a predetermined timing to generate a color video signal, which is transmitted to a video capture 226. When the video capture 226 receives the video signal, it displays an image corresponding to the received video signal on the monitor 3. At this stage, the operator can observe the surface of the paries of the patient via the monitor 3.

The operator can designate a fluorescent image by operating a switch on the operation unit. Upon operation of the switch, the CPU 221 controls the light source switching mechanism 214 to locate the mirror 213 at the fluorescent image monitoring position, and controls the rotatable filter control mechanism 216 to set the rotatable filter C in the fluorescent image observing condition. With above control, the white light emitted by the white light source 211 is shielded and the excitation light emitted by the UV light source 212 is introduced in the light guide 12b. The excitation light introduced in the light guide 12b is emerged from the illuminating lens 12a and illuminates the paries of the body cavity.

The tissues of the surface of the body cavity emits fluorescent light (which is in the green range) whose wavelength is different from that of the excitation light (which is in the ultraviolet range). It has been known that the fluorescent light emitted by the diseased tissues (i.e., suffered from cancer or a tumor) has less intensity than that emitted by normal tissues.

The fluorescent light emitted by the tissues is incident on the objective optical system 13 together with the reflected excitation light. The objective optical system 13 is provided with a cut off filter which cuts off the excitation light and allows the fluorescent light to pass through. Therefore, the fluorescent light is converged on the image receiving surface of the CCD 14, i.e., an optical image is formed on the image receiving surface of the CCD 14.

The CCD 14 converts the optical image into the image signal, which is transmitted to the pre-processing circuit 223. The pre-processing circuit 223 receives the image signal, applies processing such as amplification an the like, and applies the A/D conversion to generate digital image data. The image data is stored in Blue, Green and Red areas of the RGB memory 224 at the same time. That is, the fluorescent image is treated as a monochromatic image. The video signal processing circuit 225 retrieves the data stored in the RGB memory 224 at a predetermined timing and processes the same to generate a monochromatic video signal, which is transmitted to the video capture 226. The video capture 226 displays an image (i.e., the fluorescent image) in accordance with the received video signal. In the embodiment, the fluorescent image is displayed as a monochromatic image. It can be modified such that the fluorescent image is displayed as a color image. In this case, the color of portions of the image may be determined, for example, based on the intensity of the fluorescent light.

The operator can observe the fluorescing condition of the paries of the cavity through the monitor 3. If there is a portion whose intensity is lower than the other portion, it may be considered that a diseased portion where the cancer or tumor is formed.

When the operator identifies the portion which may be diseased by the normal image observation or fluorescent image observation, OCT images of the portion in question will be obtained. That is, when the operator identifies the portion which needs further inspection, the operator may operate the operation unit to select capturing of the tomogram. Then, the CPU 221 controls the OCT unit 23 so that the SLD 231 emits the low-coherent light beam. At the same time, the CPU 221 controls the mirror driving mechanism 234 and the scanning control circuit 235 to start capturing the tomogram. The CPU 221 also controls the timing generator 222 so that clock signals are transmitted to the RGB memory 224 and OCT memory 228, respectively. In accordance with the clock signals, the RGB memory 224 and the OCT memory 228 transmit signals to the video signal processing circuit 225 and the OCT video signal processing circuit 228 at predetermined timings, respectively.

The scanning control circuit 235 drives a scanning motor (not shown) of the OCT scanning unit 15 so that the scanning mirror 152 reciprocally rotates within a predetermined angular range. The light beams emerged from the fiber array F1 are emerged from the scanning window S by being aligned. The light beams emerged from the scanning window S converge on detection points aligned on a mutually formed detection line. As the scanning mirror 152 rotates, the detection points shift in the direction perpendicular to the mutual detection line. Thus, the OCT scanning unit 15 can perform a two-dimensional scanning operation on a rectangular area.

When the above scanning is performed, the mirror driving mechanism 234 reciprocates the reference mirror 233 in the direction parallel with the axes of the fibers of the fiber array F2 at a high speed. The mirror driving mechanism 234 and the scanning control circuit 235 operate synchronously in accordance with the reference clock signal transmitted from the timing generator 222. At every predetermined moment when the continuously moving detection line is regarded as stopped, the reference mirror 234 reciprocates once at a high speed. With this movement of the reference mirror 234, on each detection point, the objective portion is scanned in a depth direction from its surface to a predetermined depth (e.g., 2 mm deep).

At every predetermined shift of the detection line, the above-described scanning in the depth direction is performed. By executing the scanning in the depth direction, the rectangular area is two-dimensionally scanned. Thus, for all the detection points in the rectangular area, the scanning in the depth direction is performed.

It should be noted that the scanning in the depth direction starts from a position which is spaced from the surface of the paries and closer to the scanning window S to a position slightly deeper than the predetermined depth. During the scanning operation, the OCT pre-processing circuit 227 continuously monitors the output of the light detecting element 232 for all the channels. That is, the OCT pre-processing circuit 227 monitors the channels corresponding to the detection points aligned on the detection line, individually.

In the scanning operation described above, when the scanning position in the depth direction has not reached the surface of the paries, the OCT pre-processing circuit 227 does not detect a signal corresponding to the detecting point. When the scanning position has reached the surface of the paries, the OCT pre-processing circuit 227 detects a signal for the corresponding detection point. The OCT pre-processing circuit 227 regards the position, in the depth direction, at which the first signal is detected as the surface of the paries, and calibration is performed. The OCT pre-processing circuits performs the detection in the depth direction from the surface of the pairs (i.e., the depth is zero) to a position at a predetermined depth (e.g., 2 mm deep).

Then, the OCT pre-processing circuit 227 applies processing such as amplification, decoding and A/D conversion with respect to the obtained signals. The data thus obtained by the pre-processing circuit 227 is stored in the OCT memory 228. The OCT video signal processing circuit 229 retrieves the data stored in the OCT memory 228 at a predetermined timing and process the same to generate a video signal, which is transmitted to the video capture 226. The video capture 226 displays an image on the monitor 3 in accordance with the received video signal. Thus, the tomogram from the surface to the predetermined depth is displayed on the monitor 3.

Synchronously with the rotation of the scanning mirror 152, the tomogram displayed on the monitor 3 is updated. That is, at a certain moment, the image displayed on the monitor 3 is a tomogram corresponding to a certain detection line. As the detection line shifts, the tomogram displayed on the monitor 3 is also updated so as to correspond to the shifted detection line. By observing the tomogram displayed on the monitor 3 for one complete scanning of the rectangular area as well as in the depth direction, the operator can recognize the three-dimensional structure of the biotissues beneath the paries.

In the first embodiment, the video capture 226 is capable of displaying the tomogram as well as the normal image and the fluorescent image on the monitor 3 at the same time, with dividing the displaying area of the monitor 3 into three sub-areas. Specifically, the RGB memory 224 and the OCT memory 228 receives the clock signals from the timing generator 222, which is controlled by the CPU 221, and transmit the signals to the video signal processing circuit 225 and the OCT video signal processing circuit 229. Then, the video capture 226 receives the video signals from the video signal processing circuit 225 and the OCT video signal processing circuit 229, and displays the images in the respective sub-areas.

The above-described configuration of the first embodiment may be modified such that the sequentially updated tomogram may be stored in a memory. If such a memory is used, the CPU 221 can constitute a three-dimensional image based on the accumulated tomograms. In this case, the operator may designate a plane with which the three-dimensional structure is cut, and the cross sectional view thereof may be displayed on the monitor 3.

With the above-described configuration, the operator can recognize the condition beneath the paries of the cavity, an accurate and quick diagnosis can be made. Further, by the observation using only the endoscope, the operator can find the early cancer, a small tumor, or the like.

Further, since the accurate and quick diagnosis becomes possible, the operator can perform the necessary treatment of the diseased portion. For example, a forceps, laser treatment instrument or the like can be inserted through the treatment channel of the endoscope, and the treatment of the diseased portion may be performed immediately. In such a case, the burden to the patient is considerably decreased.

Second Embodiment

The second embodiment is different from the first embodiment in that the OCT unit 23 of the second embodiment is configured to have a single channel. That is, in the second embodiment, each of the light guides F1 and F2 is a single mode optical fiber, and the light detection device 232 is a photo diode. In accordance with the structure of the OCT unit 23, an OCT scanning unit 16 provided at the tip end portion of the endoscope 1 is configured to perform a two-dimensional scanning. Hereinafter, the second embodiment will be described with reference to FIGS. 6, 7 and 8.

Figure 6:
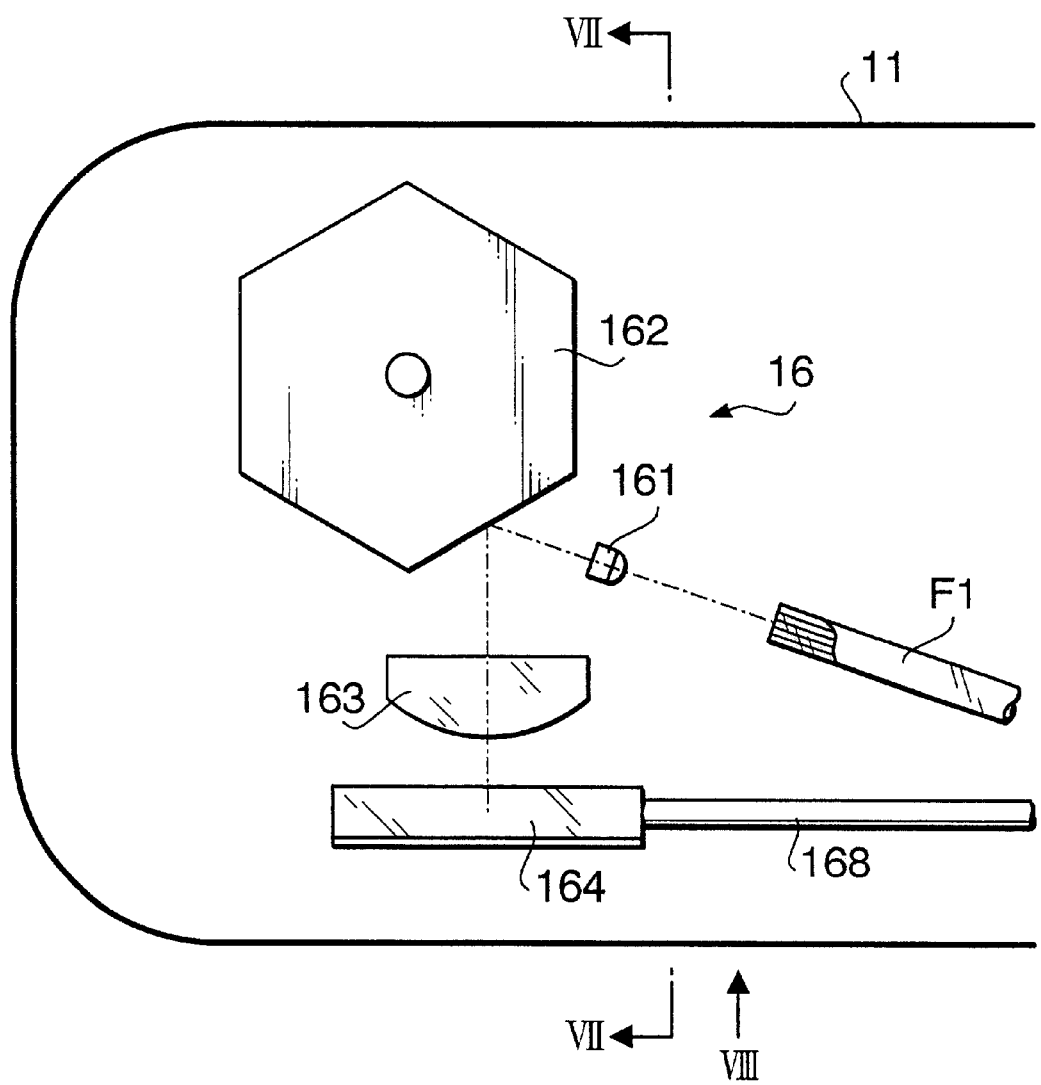
FIG. 6 shows a structure of the OCT scanning unit according to the second embodiment of the invention.
Figure 7:
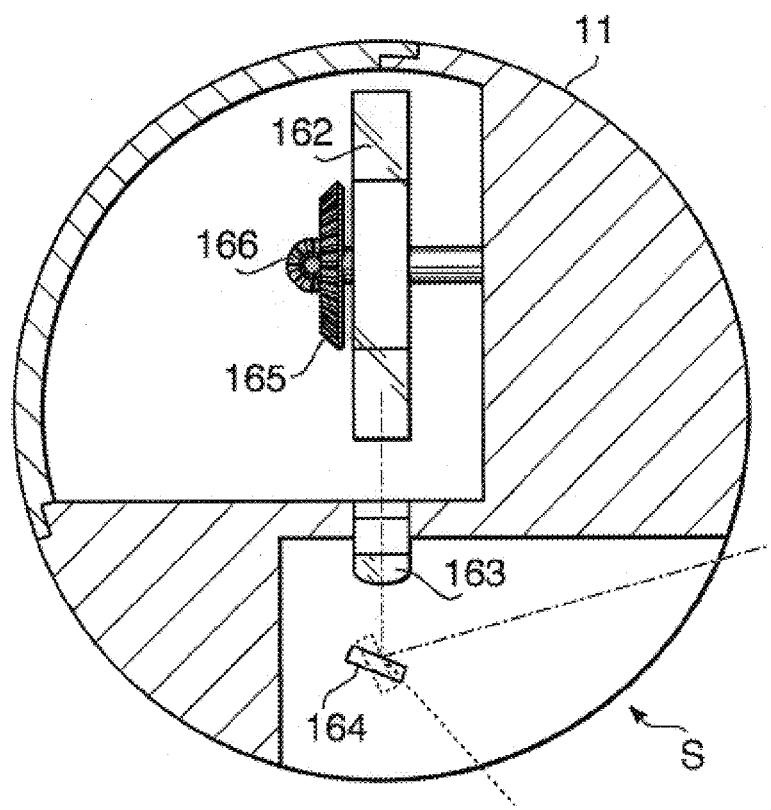
FIG. 7 is a cross section vies of the OCT scanning unit taken along line VII—VII of FIG. 6.
Figure 8:
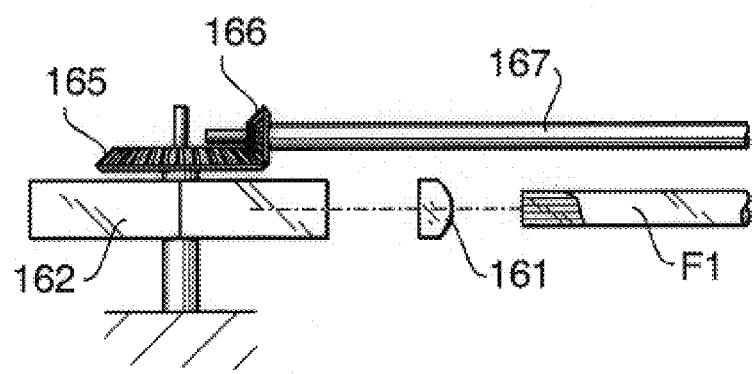
FIG. 8 is a side view of the OCT scanning unit viewed from arrow VIII of FIG. 6.

FIG. 6 is a cross sectional view of the tip end portion of the endoscope taken along a plane parallel to the axis thereof. FIG. 7 is a cross section take along line VII—VII in FIG. 6, and FIG. 8 is a side view viewed along arrow VIII in FIG. 6.

The insertion tube of the endoscope 1 has a case 11' having a substantially cylindrical appearance at the tip end portion thereof. In FIG. 6, only the outer surface of the case 11' is shown in FIG. 6, and it is not shown in FIG. 8.

The peripheral portion of the tip end surface of the case 11' is beveled smoothly. The OCT scanning unit 16 is accommodated in the case 11' at the tip side portion thereof. The first optical fiber F1 of the OCT unit 23 is inserted through the endoscope 1, tip end thereof being arranged to face the OCT scanning unit 16. The OCT scanning unit 16 includes, along the optical path thereof, a collimating lens 161, a polygonal mirror (a main scanning mirror) 162, an fθ lens 163 and an auxiliary scanning mirror 164.

The collimating lens 161 is a rotationally symmetrical plano-convex lens having a shape of a substantially rectangular solid except that one refraction surface is a convex surface as in the first embodiment. The collimating lens 161 is arranged such that the focal point on a convex surface side coincides with the center of the light emerging end surface of the fiber F1, with the optical axis being arranged in parallel with the axis of the fiber F1. Thus, the light beam emitted by the optical fiber F1 is converted into a parallel light beam by the collimating lens 161.

The polygonal mirror 162 has a shape of a hexagonal column, and the side surfaces are formed to be reflection surfaces. The polygonal mirror 162 is rotatable about the central axis thereof, the central axis being perpendicular to the central axis of the case 11'. On one end side of the polygonal mirror, a bevel gear 165 is secured. The bevel gear 165 is engaged with another bevel gear 166, which is secured to a first rotary shaft 167 extending in parallel with the central axis of the case 11'. The rotary shaft 167 is connected to a not shown main scanning motor.

The fθ lens 163 is a plano-convex lens having a shape of a substantially a rectangular solid except that one refraction surface is a convex surface. The fθ lens 163 is arranged such that the wider side surfaces extend in a direction perpendicular to the central axis of the polygonal mirror 162, with a planer surface, which is perpendicular to the optical axis, facing the polygonal mirror 162. The planer surface of the fθ lens 163 is parallel to the central axis of the case 11'. The fθ lens 163 and the collimating lens 161 constitute an a focal optical system. The fθ lens 163 receives the parallel beam reflected by the polygonal mirror 162 and converges the beam on a predetermined line. The beam moves (i.e., scans) on the predetermined line at a constant speed.

The auxiliary scanning mirror 164 has a rectangular reflection surface. The auxiliary scanning mirror 164 is arranged such that the central axis of the reflection surface in the longitudinal direction is parallel with the central axis of the case 11', and the reflection surface faces a surface, which has a power, of the fθ lens 163.

One end (i.e., a proximal end) of the auxiliary scanning mirror 164 is secured to a second rotary shaft 168, which is arranged in parallel with the central axis of the case 11'. The rotary shaft 168 is connected to a not shown auxiliary scanning motor. By driving the auxiliary scanning motor, the auxiliary scanning mirror 164 can be rotated reciprocally about the shaft 168 within a predetermined angular range.

The light beam emerged from the tip end of the optical fiber F1 is collimated by the collimating lens 161, and is incident on the polygonal mirror 162. The main scanning motor rotates the first shaft 167. Then, through the engagement of the bevel gears 166 and 165, the polygonal mirror 162 is rotated. The light beam incident on the polygonal mirror 162 is deflected by the reflection surfaces of the polygonal mirror 162, converged by the fθ lens 163 and scans on the auxiliary scanning mirror 164 in the longitudinal direction thereof. The scanning beam is reflected by the auxiliary scanning mirror 164 and converged on the paries of the human cavity.

A beam deflected by on reflection surface of the polygonal mirror 162 forms one scanning line (i.e., a main scanning line) on the paries. The auxiliary scanning mirror 164 rotates by a predetermined amount while one main scanning is performed. Therefore, the next main scanning line formed on the paries will be shifted in the auxiliary scanning direction, which is perpendicular to the main scanning line, by a predetermined amount with respect to the previous main scanning line. As the procedure is repeated, the main scanning line is gradually shifted in the auxiliary scanning direction, and finally, a predetermined rectangular area can be scanned.

The light beam reflected by the paries proceeds in the opposite direction with respect to the incident beam, and then enters the endoscope 1. That is, the reflection light beam (i.e., the detection light beam) proceeds from the auxiliary scanning mirror 164, the fθ lens 163, the polygonal mirror 162, and the collimating lens 161 in this order, and then impinges on the optical fiber F1.

The mirror driving mechanism 234 of the OCT unit 23 reciprocally drives the reference mirror 233 in the direction parallel to the axis of the optical fiber F2. That is, at every moment when the polygonal mirror 162 and the auxiliary scanning mirror 164 are regarded as being stopped, the reference mirror 233 reciprocates once. With this movement, at one scanning point, a scanning in the depth direction, i.e., from the surface of the paries to a predetermined depth (e.g., 2 mm deep) can be performed.

By repeating the above scanning in the depth direction, for all the scanning points on the certain main scanning line, the scanning in the depth direction can be performed.

Further, the similar scanning is performed for every main scanning line, the scanning in the depth direction can be done for all the scanning points in the rectangular scanning area.

The signal output by the light detecting device 232 is processed by the OCT pre-processing circuit 227, the OCT memory 228, the OCT video signal processing circuit 229 and the video capture 226, and then the tomogram is displayed on the monitor 3.

Third Embodiment

The third embodiment is different from the first embodiment in that an OCT scanning unit 17 provided with a polygonal mirror 172 is employed. The third embodiment will be described with reference to FIGS. 9, 10 and 11.

Figure 9:
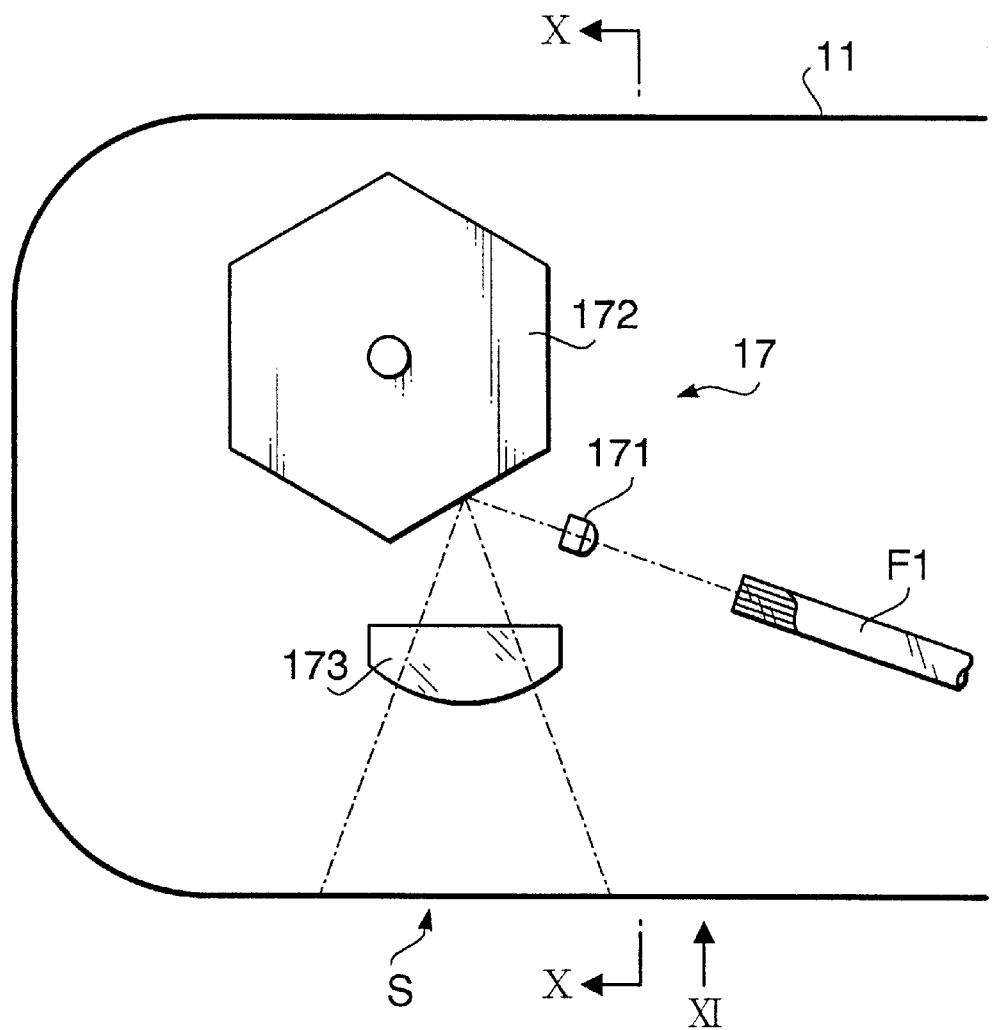
FIG. 9 shows a structure of the OCT scanning unit according to the third embodiment of the invention.
Figure 10:
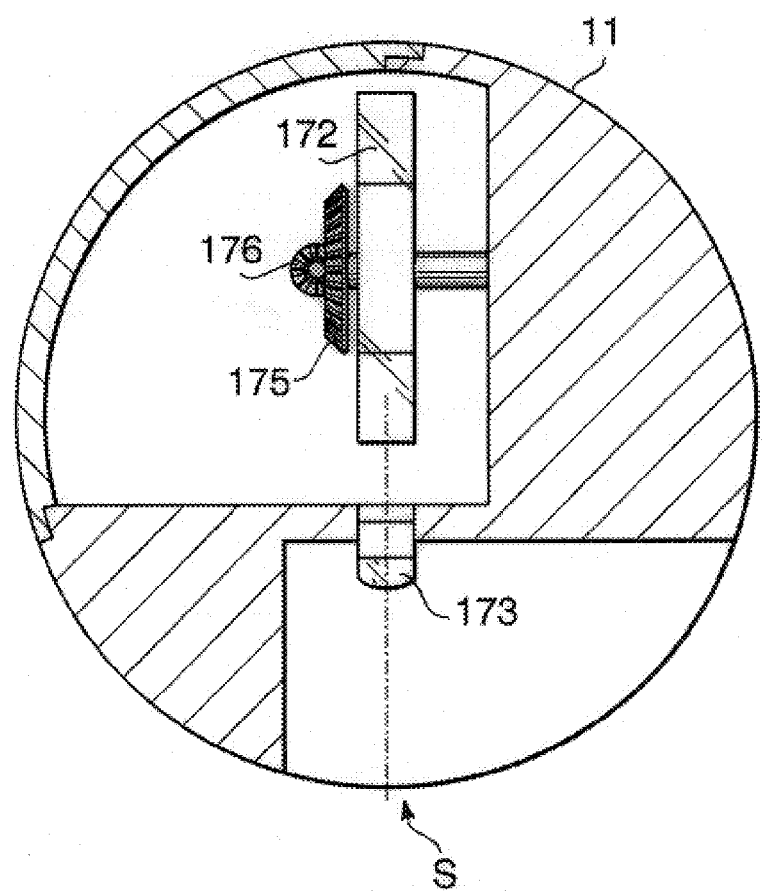
FIG. 10 is a cross section vies of the OCT scanning unit taken along line X—X of FIG. 9.
Figure 11:
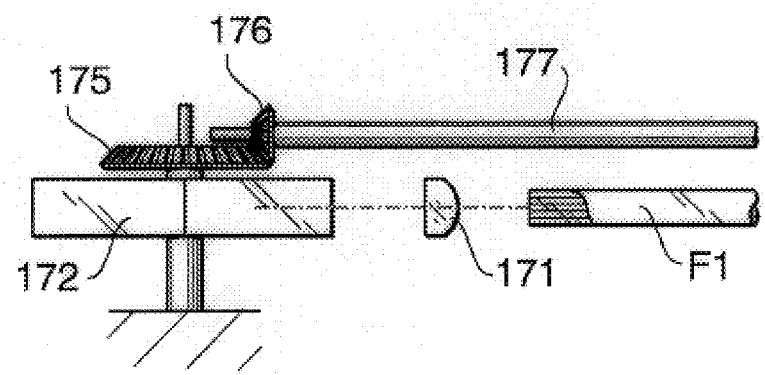
FIG. 11 is a side view of the OCT scanning unit viewed from arrow XI of FIG. 9.

FIG. 9 is a cross sectional view of the tip end portion of the endoscope taken along a plane parallel to the axis thereof. FIG. 10 is a cross section take along line X—X in FIG. 9, and FIG. 11 is a view viewed along arrow XI in FIG. 9.

The insertion tube of the endoscope 1 has a case 11' having a substantially cylindrical appearance at the tip end portion thereof. In FIG. 9, only the outer surface of the case 11' is shown, and it is not shown in FIG. 11.

The peripheral portion of the tip end surface of the case 11' is beveled smoothly. The OCT scanning unit 17 is accommodated in the case 11' at the tip side portion thereof. The first optical fiber array F1 of the OCT unit 23 is inserted through the endoscope 1, tip end thereof being arranged to face the OCT scanning unit 17. The fiber array F1 is constituted such that a line passing the center of the end surface of each optical fiber is perpendicular to the central axis of the case 11'.

The OCT scanning unit 17 includes, along the optical path thereof, a collimating lens 171, a polygonal mirror 172 and an fθ lens 173.

The collimating lens 171 is a rotationally symmetrical plano-convex lens having a shape of a substantially rectangular solid except that one refraction surface is a convex surface. The collimating lens 171 is arranged such that the focal point on a convex surface side coincides with the center of light emerging end surface of the fiber array F1, with the optical axis being arranged in parallel with the axis of each fiber of the fiber array F1. Thus, the light beams emitted by the optical fibers of the fiber array F1 are converted into parallel light beams by the collimating lens 171. The principal ray of the central fiber of the fiber array F1 coincides with the optical axis of the collimating lens 171. However, principal rays of the other fibers intersect with the optical axis of the collimating lens at the object side focusing point (exit pupil) of the collimating lens 171. The exit pupil coincides with the center of the scanning mirror 172.

The polygonal mirror 172 has a shape of a hexagonal column, and the side surfaces are formed to be reflection surfaces. The polygonal mirror 172 is rotatable about the central axis thereof, the central axis being perpendicular to the central axis of the case 11'.

On one end side of the polygonal mirror, a bevel gear 175 is secured. The bevel gear 175 is engaged with another bevel gear 176, which is secured to a first rotary shaft 177 extending in parallel with the central axis of the case 11'. The rotary shaft 177 is connected to a not shown main scanning motor.

The fθ lens 173 is a plano-convex lens having a shape of a substantially rectangular solid except that one refraction surface is a convex surface. The fθ lens 173, together with the collimating lens 171, constitutes an a focal optical system. The fθ lens 173 is arranged such that the convex surface faces the scanning window S. The optical axis of the fθ lens 173 is perpendicular to the plane on which the fiber array F1 is arranged. The fθ lens 173 converges each of the parallel beams reflected by the scanning mirror 172 on a line perpendicular to the surface of FIG. 9, outside the endoscope 1, at an even interval.

With the above construction of the OCT scanning unit 17, each light beam, which is a diverging beam, emitted by each fiber of the fiber array F1 is directed to the collimating lens 171, with the principal rays aligned on a same plane. The collimating lens 171 collimates the incident beams, and emits the collimated beams with inclined toward the optical axis.

A principal ray of each parallel beam emitted by the collimating lens 171 intersects with optical axis at the center of the scanning mirror 172. Therefore, on downstream of the scanning mirror 172, an arrangement of the parallel beams is reversed (in FIG. 11, the arrangement in up-and-down direction is reversed). The parallel light beams reflected by the scanning mirror 172 are directed to the fθ lens 173. The fθ lens 173 converges the incident beams on a predetermined line outside the endoscope 1 and are arranged evenly spaced from each other.

If the endoscope 1 is located to face the paries of the cavity, the beams emitted from the fθ lens 173 are incident on the paries. The points on the paries on which the beams are incident are the detection points, and a line connecting the detection points is a detection line segment. The polygonal mirror 172 is rotated at a constant speed, and therefore, the detection line segment defined by the beams passed through the fθ lens 173 moves, on the paries, in a direction perpendicular to the detection line segment at a constant speed.

The light beams emitted toward the paries are reflected thereby, and proceed along the opposite direction. That is, each beam proceeds from the fθ lens 173, the polygonal mirror 172, the collimating lens 171 in the order and then is incident on each optical fiber of the fiber array F1.

The mirror driving mechanism 234 of the OCT unit 23 drives the reference mirror 233 to reciprocate in the direction parallel to the axis of each optical fiber of the fiber array F2 at a high speed. That is, at every moment when the polygonal mirror 172 is regarded as being stopped, the reference mirror 234 reciprocates once. Thus, for a detection line segment, at each detection point, from the surface of the paries to a predetermined depth (e.g.,2 mm deep), a scanning is performed in the depth direction.

As the polygonal mirror 172 rotates by a predetermined amount, the detection line segment shifts in the direction perpendicular to the detection line segment by a predetermined amount. Since the reference mirror 234 reciprocate once at this stage, scanning in the depth direction is performed at the detection points on the new detection line segment. As this procedure is repeated, the detection line segment shifts gradually, and for all the detection points in a predetermined rectangular area, the scanning in the depth direction are performed.

The output of the light detection device 232 is transmitted to the OCT pre-processing circuit 227, and then, to the OCT memory 228, OCT video signal processing circuit 229, and the video capture 226, and an image is displayed on the monitor 3.

As explained above with reference to three embodiments, according to the present invention, tomogram of a three-dimensional portion which is defined from a surface of a rectangular area on an object to a predetermined depth thereof can be obtained. Therefore, even if there is a diseased portion beneath the surface of the object, it can be identified accurately and quickly.

The present disclosure relates to the subject matter contained in Japanese Patent Application No. HEI 11-225055, filed on Aug. 9, 1999, which is expressly incorporated herein by reference in its entirety.

What is claimed is:

1. An endoscope system, comprising:

a first light guide;

a second light guide;

an optical coupler for optically coupling said first and second light guides;

a low-coherent light source that emits a low-coherent light beam, said low-coherent light source being provided at a proximal end side of one of said first and second light guides, the light emitted by said low-coherent light source being incident on said one of said first and second light guides;

a scanning unit comprising an fθ lens and at least one of a rotatable flat mirror and a rotatable polygonal mirror, wherein at least one light beam emerged from said first light guide is deflected by said at least one of said rotatable flat mirror and said rotatable polygonal mirror to scan on a predetermined surface of said object through said fθ lens, at least one light beam reflected by said object passes through said fθ lens and is deflected by said at least one of said rotatable flat mirror and said rotatable polygonal mirror to be incident on said first light guide as a detection beam;

a reflector that reflects at least one light beam emerged from said second light guide to said second light guide as a reference beam;

an optical path length adjusting system that relatively changes a length of an optical path length from said optical coupler to said object via said first light guide and an optical path length from said optical coupler to said reflector via said second light guide;

a light detecting device provided at a proximal end side of the other of said first and second light guides, said light detecting device detecting interfered beam generated due to interference between said reference beam and said detection beam; and a signal processing system that generates a tomogram based on the signal detected by said light detecting device when said optical path length adjusting system and said scanning unit operate.

2. The endoscope system according to claim 1, wherein said first light guide includes a plurality of optical paths, wherein said second light guide includes a plurality of optical path, the number of the optical paths included in said second light guide being equal to the number of the optical path included in said first light guide, wherein said optical coupler couples said plurality of optical paths included in said first light guide with said plurality of optical paths included in said second light guide, respectively, said scanning unit causes the light beams emitted from the plurality of optical paths of said first light guide to be incident on the object with the plurality of light beams being aligned such that a detection line is formed on the object, said scanning unit shifting the detection line in a direction perpendicular to said detection line so as to scan a predetermined two-dimensional area, the plurality of beams reflected by the object being directed to said plurality of optical paths of said first light guide via said scanning unit.

3. The endoscope system according to claim 2, wherein each of said first and second light guides is composed of a fiber array having a plurality of single-mode optical fibers arranged in parallel.

4. The endoscope system according to claim 2, wherein said scanning unit includes a deflector that deflects the plurality of light beams emitted from the tip of the plurality of optical paths of the first light guide toward the object with the plurality of beams aligned in parallel, and shifts the detection line in the direction perpendicular to said detection line with the plurality of beams remained to be aligned in parallel.

5. An endoscope system comprising:

a first light guide;

a second light guide;

an optical coupler for optically coupling said first and second light guides;

a low-coherent light source that emits a low-coherent light beam, said low-coherent light source being provided at a proximal end side of one of said first and second light guides, the light emitted by said low-coherent light source being incident on said one of said first and second light guides;

a scanning unit that causes the light beam emerged from said first light guide to scan on a predetermined surface of said object, said scanning unit directing the light beam reflected by the object to said first light guide as a detection light beam;

a reflector that reflects a light beam emerged from said second light guide to said second light guide as a reference beam;

an optical path length adjusting system that relatively changes a length of an optical path length from said optical coupler to said object via said first light guide and an optical path length from said optical coupler to said reflector via said second light guide;

a light detecting device provided at a proximal end side of the other of said first and second light guides, said light detecting device detecting interfered beam generated due to interference between said reference beam and said detection beam; and a signal processing system that generates a tomogram based on the signal detected by said light detecting device when said optical path length adjusting system and said scanning unit operate;

wherein each of said first and second light guides includes a single optical path, and wherein said scanning unit includes a main scanning device which shifts the incident position of the beam, on the object, emitted by the first light guide in a main scanning direction, and an auxiliary scanning device which shifts the incident position of the beam, on the object, emitted by the first light guide in an auxiliary scanning direction which is perpendicular to the main scanning direction.

6. The endoscope system according to claim 5, wherein: said low-coherent light source emits a low-coherent light beam; and one of said main scanning device and said auxiliary scanning device is a rotatable polygonal mirror, and the other of said main scanning device and said auxiliary scanning device is a rotatable flat mirror; and said scanning unit further comprises an fθ lens, wherein light beams deflected by said scanning unit are incident on the object through said fθ lens.

7. The endoscope system according to claim 1, wherein said signal processing system generates a tomogram of the object, said tomogram corresponding to an area from a surface of the object to a predetermined depth therefrom.

8. The endoscope system according to claim 1, wherein said optical path length adjusting system is configured to move said reflector in at least one of a direction toward and away from a tip of said second light guide to vary the optical path length from said optical coupler to said reflector via said second light guide relative to the optical path length from said optical coupler to said object vial said firs light guide.

9. The endoscope system according to claim 1, wherein said low-coherent light source includes a super-luminous diode.

10. The endoscope system according to claim 1, further comprising:

an illuminating optical system configured to emit at least one of visible light and excitation light which causes biotissues to fluoresce, to the object;

an objective optical system that converges the light from the surface of the object to form an object image; and an image capturing system that captures the optical image formed by said objective optical system.

11. An endoscope system comprising:

a first light guide;

a second light guide;

an optical coupler for optically coupling said first and second light guides;

a low-coherent light source that emits a low-coherent light beam, said low-coherent light source being provided at a proximal end side of one of said first and second light guides, the light emitted by said low-coherent light source being incident on said one of said first and second light guides;

a scanning unit that causes the light beam emerged from said first light guide to scan on a predetermined surface of said object, said scanning unit directing the light beam reflected by the object to said first light guide as a detection light beam;

a reflector that reflects a light beam emerged from said second light guide to said second light guide as a reference beam;

an optical path length adjusting system that relatively changes a length of an optical path length from said optical coupler to said object via said first light guide and an optical path length from said optical coupler to said reflector via said second light guide;

a light detecting device provided at a proximal end side of the other of said first and second light guides, said light detecting device detecting interfered beam generated due to interference between said reference beam and said detection beam; and a signal processing system that generates a tomogram based on the signal detected by said light detecting device when said optical path length adjusting system and said scanning unit operate;

an illuminating optical system comprising:
   a) a visible light source emitting visible light; and
   b) an excitation light source emitting excitation light;
an objective optical system that converges the light from the surface of the object to form an object image;
an image capturing system that captures the optical image formed by said objective optical system;
a light source switching system that selects one of the visible light and the excitation light and causes the selected one of the visible light and excitation light to be incident on said illuminating optical system, wherein said objective optical system forms a light image of the object when the visible light is incident in said illuminating optical system, and wherein said objective optical system forms a fluorescent light image of the object when the excitation light is incident in said illuminating optical system.

12. The endoscope system according to claim 10, further comprising a displaying device that displays the object image captured by said image capturing system, and the tomogram generated by said signal processing system.

* * * * *